United States Patent [19]

Pusey et al.

[11] Patent Number: 4,764,371
[45] Date of Patent: Aug. 16, 1988

[54] **POSTHARVEST BIOLOGICAL CONTROL OF STONE FRUIT BROWN ROT BY *BACILLUS SUBTILIS***

[75] Inventors: Paul L. Pusey, Warner Robins, Ga.; Charles L. Wilson, Shepherstown, W. Va.

[73] Assignee: The United States of America as represented by the Secretary of Agriculture, Washington, D.C.

[21] Appl. No.: 797,538

[22] Filed: Nov. 13, 1985

Related U.S. Application Data

[63] Continuation-in-part of Ser. No. 606,069, May 1, 1984, abandoned.

[51] Int. Cl.$^4$ ..................... A61K 39/07; A01N 63/00; A23B 7/00
[52] U.S. Cl. ........................................ 424/93; 424/92; 426/133; 426/310; 426/335; 435/832; 435/839
[58] Field of Search ................... 424/92, 93; 435/832, 435/839; 426/133, 310, 335

[56] References Cited

PUBLICATIONS

M. J. Thirumalachar and Muriel J. O'Brien; *Plant Disease Reporter;* vol. 61; No. 7, (Jul. 1977).
R. S. Utkhede and J. E. Rahe; *The American Phytopathological Society;* 73; pp. 890–893; (1983).
V. H. Lengkeek and J. D. Otta; *Proc. S. C. Acad. Sci.;* vol. 58; (1979).
Youssef Abdel Ghani Youssef and Moustafa El Sayed; "Investigations of the Biological Control of Fusarium Cotton Wilt by *Bacillus subtilis* Cohn".
T. R. Swinburne andf Averil E. Brown; *Ann, Appl. Biol.;* "A Comparision of the Use of *Bacillus subtilis* With Conventional Fungicides for the Control of Apple Canker (*Nectaria galligena*)"; (1976).
T. R. Swinburne; *Microflora of Apple Leaf Scars in Relation to Infection by Nectaria galligena*" *Trans. Br. Mycol. Cos.;* 60(3), 380–493 (1973).
John Dunleavy; "Control of Damping-Off of Sugar Beet by *Bacillus subtilis*"; *Phytopathology;* 45; pp. 252–258; (1955).
C. Jacyn Baker, J. R. Stavely, C. A. Thomas, Myron Sasser and Janet S. Machall; "Inhibitory Effects of *Bacilklus subtilis* on *Uromyces phaseoli* and on Development of Rust Pustles on Bean Leaves" *Phytopathology;* 73(8); pp. 1148–1152 (1983).
Thor Kommedahl and 1-Pin Chang Mew; "Biocontrol of Corn Root Infection in the Field by Seed Treatment With Antagonists" *Phytopathology;* vol. 65; pp. 296–300 (1975).

*Primary Examiner*—Morton Foelak
*Assistant Examiner*—Garnette D. Draper
*Attorney, Agent, or Firm*—M. Howard Silverstein; David G. McConnell; Raymond C. Von Bodungen

[57] ABSTRACT

A method for treating postharvest stone fruit to prevent or inhibit brown rot of stone fruit with effective amounts of any of the following active ingredients in a carrier is disclosed: *Bacillus subtilis* B-3; *Bacillus subtilis* B-3 in combination with 2,6-dichloro-4-nitroaniline; *Bacillus subtilis* B-3 in combination with water based wax; and, *Bacillus subtilis* B-3 in combination with paraffin and mineral oil base.

10 Claims, 1 Drawing Sheet

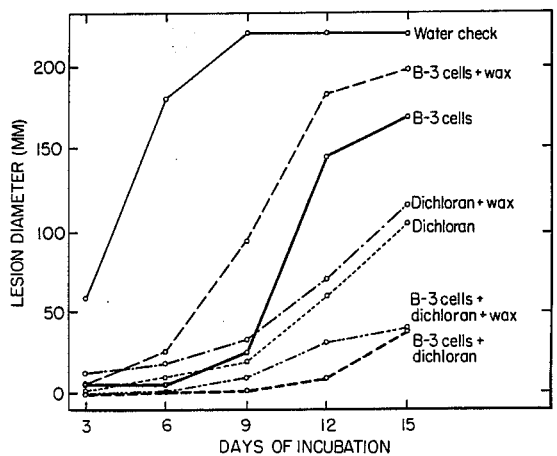

Additive effect against postharvest brown rot when *Bacillus subtilis* B-3 cell suspensions and dicloran were combined and applied to peach fruit. Treatments were made to wounded fruit with or without water-base wax produced by Decco Tiltbelt Division of Pennwalt Corp. Following treatment and fungal-spore challenge, fruit were incubated in moist chamber at 20°C for 3–15 days.

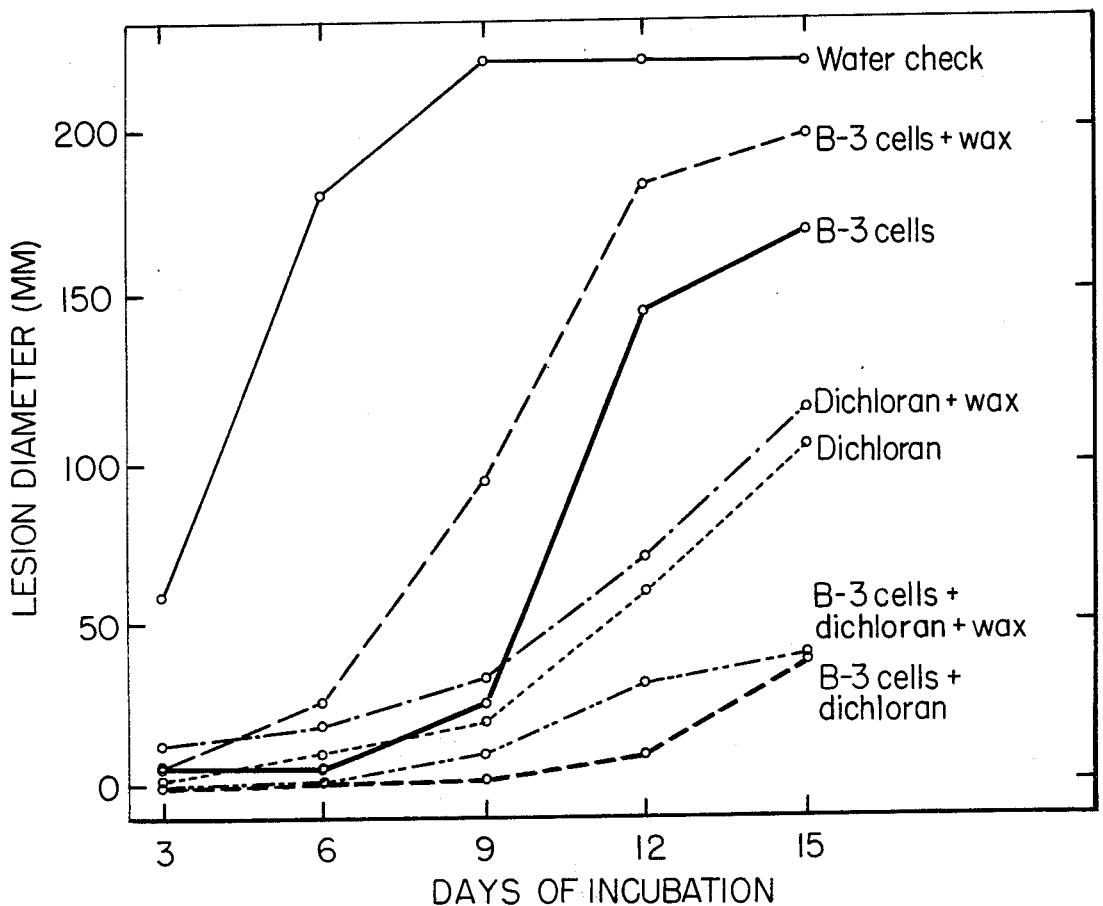

Additive effect against postharvest brown rot when Bacillus subtilis B-3 cell suspensions and dicloran were combined and applied to peach fruit. Treatments were made to wounded fruit with or without water-base wax produced by Decco Tiltbelt Division of Pennwalt Corp. Following treatment and fungal-spore challenge, fruit were incubated in moist chamber at 20°C for 3-15 days.

FIGURE 1

POSTHARVEST BIOLOGICAL CONTROL OF STONE FRUIT BROWN ROT BY *BACILLUS SUBTILIS*

CROSS REFERENCE TO RELATED APPLICATIONS

This is a Continuation-In-Part of application Ser. No. 606,069, filed May 1, 1984 abandoned.

BACKGROUND OF THE INVENTION (1) Field of the Invention

This invention relates to a method of biologically controlling a postharvest disease on stone fruit.

(2) Description of the Prior Art

*Bacillus subtilis* strains have been shown in the past to biologically control various plant diseases in agricultural plants. Some of the examples are as follows:

Thirumalachar and O'Brien showed that a strain of *Bacillus subtilis* inhibited the growth in vitro of *Macrophomina phaseolina* and *Botryodiplodia solanituberosi*, pathogens that cause charcoal rot of potatoes. In field studies, preplant treatment of seedpieces and whole tubers with this bacterial antagonist reduced the frequency of charcoal rot at harvest. (*Plant Dis. Reptr.*, 61:543–546 (1977)).

Utkhede and Rahe undertook a study to identify stable antagonists to isolates of *Sclerotium cepivorum* for biological control of onion white rot. Significant differences in antagonism were detected among the antagonists. The order of antagonists, ranked according to antagonism and ability to control onion white rot, and depended on the isolate of *S. cepivorum* being tested. However, the statistical model quantitatively identified useful characteristics in the B2 isolate of *B. subtilis*. This indicates that the bacterial antagonist B2 has a potential for biological control of onion white rot over a range of isolates of *S. cepivorum* from five countries. (*Phytopathology* 73:890–893 (1983)).

Spring wheat seed (*Triticum aestivum* "Protor") treated with one of several species of the genus Bacillus was planted in hill plots or in pots inoculated with one of six organisms pathogenic to wheat. Yields and root lesion counts were not affected by the seed treatments. (Lengkeek and Otta; *Proc. S. D. Acad. Sci.*, 58:144–156 (1979)).

In a factorialized field trial cells of *B. subtilis* or phenylmercuric nitrate (PMN) were applied as sprays in autumn to manually defoliated apple trees, C. Bramley's Seedling, artificially infected with *Nectria galligena*. Trees were additionally sprayed with dithianon at intervals in May and June or left unsprayed at this time. *B. subtilis* in conjunction with dithianon, and PMN with dithianon were equally effective in the control of canker over a 2-yr period. Dithianon alone gave some control, as did PMN but *B. subtilis* was not effective without additonal applications of dithianon. (Swinburne and Brown; *Ann. Appl. Biol.* 82, 365–368 (1976)).

Bacterial colonies are more frequently isolated from leaf scars sampled in December than earlier or later, and among the species present *B. subtilis* has been found to be highly antagonistic to *N. galligena* in vitro. Artificial inoculation of leaf scars with *B. subtilis* immediately after leaf fall reduced the frequency of isolation of all fungal species and reduced the incidence of canker when shoots were inoculated with *N. galligena* either 24 h after *B. subtilis* or the following April, but had little effect on their infection with *N. galligena* in May, when the primary protective layer was found to be shed. More cankers resulted from inoculation in May than in April. The numbers of bacterial colonies recovered from leaf scars inoculated with *B. subtilis* remained relatively constant from autumn until the primary protective layer was shed the following summer. (Swinburne; *Trans. Br. mycol. Soc.* 60:389–403 (1973)).

Dunleavy demonstrated that when *B. subtilis* was added to sterile soil inoculated with *Rhizoctonia sp.*, the incidence of damping-off was reduced considerably in comparison with that which occurred in soil that did not contain the bacteria. (*Phytopathology* 45:252–258 (1955)).

Microscopic observations of bean leaves treated with *B. subtilis* showed urediospore germination was greatly reduced and no normal germ tubes were produced. Baker et al.; *Phytopathology*; Vol 73, No.8 (1983)).

Kernels of corn (*Zea mays*) of three hybrids were coated with *B. subtilis*, *Chaetomium globosun*, or captan and planted in the field in three successive years. Stands increased 9 and 14 days after planting and at season's end for all hybrids with *Chaetomium* and captan treatments and for one hybrid with *B. subtilis* treatment. Treatments hastened attainment of an approximate 95% stand by 1–3 days depending on hybrid and treatment. Stalk rot and breakage were less with the organism and captan-coated than with non-coated Kernels. The stalk rot pathogen most frequently isolated was *Fusarium roseum* "Graminearum". Grain yields per treatment were higher for kernels coated with captan in all years, for those coated with *C. globosum* for 2 of 3 years and for those coated with *B. subtilis*, only 1 year, than for kernels not coated. (Kommedahl and Mew; *Phytopathology* 65:296–300 (1975)).

There is no prior art which teaches the use of *B. subtilis* for control of Brown rot on stone fruit.

SUMMARY OF THE INVENTION

A method for biologically controlling or inhibiting brown rot on postharvest stone fruit is disclosed. Postharvest stone fruit is coated with an effective amount of *Bacillus subtilis* B-3 bacteria in a carrier to prevent or control the growth of brown rot on the fruit.

Although effects of some strains of *B. subtilis* on plant diseases have been previously demonstrated, all previous cases involved application of the bacterium to plants or soil in the field or greenhouse environment and none of the prior art recognized that *B. subtilis* could be used for controlling Brown Rot. Applicants are the first to identify and use the B-3 strain of *B. subtilis* in a postharvest environment to control decay of a stored stone fruit product. Their's was the first known use of such a bacterial treatment under postharvest conditions. As a result of their discovery such treatments have become widely used in commerce. This advance in the state of the art was particularly noteworthy for the following reasons:

(1) No biological pesticide had ever been applied to an agricultural product after harvest for disease control.

(2) It is applicants discovery and isolation of the B-3 strain of *B. subtilis* which makes the control of Brown rot on the stone fruit possible.

(3) It is well known in the art that one cannot predict activity of a biological control agent because any minor difference in plant host, pathogen or biocontrol agent can produce a totally different result.

(4) Under postharvest conditions stone fruit are stored at refrigerated temperatures which are lower than the minimum temperature required for growth and antibiotic production of *B. subtilis*. Therefore, the growth or virulance of the fungal pathogen at these lower storage temperatures was totally unexpected.

(5) Additionally, it was totally unexpected for *B. subtilis* to: (a) undergo normal respiration when covered with or incorporated into waxes (water or paraffin and mineral oil base) which are used as carriers in coating of fruit in commercial fruit-packing operations and (b) adapt to the microenvironment on wax-coated fruit.

(6) Furthermore, since mycrobiocides, such as hypochlorous acid, are mixed in the hydrocooling water of commercial packing houses, one would not have expected *B. subtilis* (B-3) to be compatible with such chemicals.

(7) The acidic environment of fruit surface (pH 3-4) is very nonconducive for growth and antibiotic production by *B. subtilis*.

BRIEF DESCRIPTION OF THE DRAWINGS

FIG. 1 is a graft showing compatibility results when *B. subtilis* B-3 is tested with dichloran.

DESCRIPTION OF THE PREFERRED EMBODIMENTS

Strain B-3 of *B. subtilis* is on deposit as NRRL B-15813 at: ARS Patent Collection, Northern Regional Research Center, 1815 North University Street, Peoria, Illinois 61604.

EXAMPLE 1

To demonstrate applicants invention the B-3 strain of *Bacillus subtilis* (Cohn) Prazmowski was tested in the laboratory for antagonism against *Monilinia fructicola* on wounded stone fruit. The effect of B-3 on fruit decay was compared to that of one other *B. subtilis* strain and three other bacterial species. Peaches, nectarines, apricots and plums were sprayed with bacterial suspensions, inoculated 1-2 hr later with spores of *M. fructicola* and then held in moist chambers at 18-°24° C. Only the B-3 strain reduced brown rot on all fruit types. When varying concentrations of B-3 were tested on peaches, brown rot development was retarded by $10^6$ and $10^7$ colony forming units (CFU) per milliliter. At $10^8$, none of the fruit became infected with *M. fructicola* but decayed after 9 days due to the presence of other fungi. Decay was reduced regardless of the level of inoculum or the isolate of *M. fructicola* used and was effective at all temperatures which permitted fungal growth after 5 days incubation (10°-30° C.) The mechanism of B-3 activity appears to involve production of an antifungal substance since the sterile culture filtrate protected fruit from rot. The filtrate retained activity after being autoclaved at 15 psi and 120° C. for 15 min.

MATERIALS AND METHODS

Strain B-3 of *B. subtilis* was isolated at Kearneysville, WV, and is presumed to have come from either the soil or the surface of apple roots since it appeared on a medium to which root sections had been added for the purpose of isolating pathogenic fungi. Other bacteria were: *Pseudomonas cepacia* Burkholder (Pc-41) and *P. fluorescens* Migula (Pf-21) obtained from Harvey Spurr, USDA-ARS, Tobacco Research Laboratory, Oxford, NC 27565; *B. subtilis* morphotype globigii (B-1849) from William Haynes, USDA, ARS, Fermentation Laboratory, Peoria, IL 61604; and *B. thuringiensis* Berlinder (HD-1) from Howard T. Dulmage, USDA-ARS, Cotton Insects Research Laboratory, Brownsville, TX 78520. An isolate of *M. fructicola* (WV-20) collected from a peach orchard, was used as inoculum.

Test fruit were from orchard trees at the Appalachian Fruit Research Station. During fruit development, trees had been sprayed only with captan as a fungicide at 5.6 kg per hectare. Before being tested in the laboratory, fruit were washed in water with 0.05-0.2% Tween-20. Nectarine, apricot and plum clones used Harko, V66022 and BY68-87, respectively. Peach clones used, depending on availability, were LaGem, Norman, Loring, Mountain Gold and B70446. Fruit were collected at firm ripe maturity similar to those normally harvested commercially for storage or transit.

Antagonism tests. In vitro tests were performed on potato dextrose agar (PDA) and nutrient yeast dextrose agar (NYDA; 8 g nutrient broth, 5 g yeast, 10 g dextrose, and 15 g agar per liter of medium) in 9 cm petri plates. Plates were streaked across the center with the bacterium incubated at 25° C. for 2 days, then sprayed with $10^5$ spores per milliliter aqueous suspension of *M. fructicola*. After 3 days of additional incubation, width of the inhibition zone was measured for each of six plates per strain.

The bacteria were applied in suspension to wounded surfaces of peaches, nectarines, apricots and plums, and fruit were subsequently sprayed with spores of *M. fructicola*. Bacteria were initially transferred from nutrient agar slants (stored at 5° C.) to 50 ml of nutrient yeast dextrose broth, (NYDB; 8 g nutrient broth, 5 g yeast, and 10 g dextrose per liter) in 250 ml flasks. After incubation on a gyratory shaker at 200 rpm and 30° C. for 24 hr, 5 mls of the liquid culture were transferred to 1-liter Erlenmeyer flasks containing 250 ml of NYDB. After 3 days at 200 rpm and 30° C., bacterial cells were harvested by centrifugation at 6,000 X g for 20 min and resuspended in water.

Fruit were wounded with a dissecting knife that had been forced through a cork stopper so that the protruding point would make a wound approximately 3 mm in diameter and 3 mm deep. Ten fruit per treatment were sprayed to run-off with bacterial suspensions $10^7$ colony forming units (CFU) per milliliter and control fruit were sprayed with water. For comparison, an additional treatment was made with 300 ppm benomyl (active ingredient of Benlate 50 W). After drying for 1-2 hr, fruit surfaces were sprayed-inoculated with a $10^5$ spores per milliliter aqueous suspension of *M. fructicola*. The fruit were then held at 18°-24° C. in moist chambers. After 2 days for plums and 3 days for all other fruit, disease development was determined by measuring the distance between two margins of the decay lesion through the point of inoculation. Although this distance follows an arc rather than a straight line, we refer to it here (and in other Examples) as the lesion diameter. Figures were corrected subtracting the 3.0-mm wound diameter. Various concentrations of bacteria ($10^5$ to $10^9$ CFU) per milliliter were later tested on peach fruit against $10^5$ fungal spores per milliliter.

Procedures for subsequent tests with *B. subtilis* were the same as above, except where specified. Strain B-3 was challenged with $10^3$ to $10^7$ spores per milliliter of *M. fructicola* It was also tested against four other isolates of *M. fructicola* (at $10^5$ spores per milliliter) from different areas of the United States (California, Missouri, New York and South Carolina). The effect of temperature on B-3 antagonism was studied by holding fruit in moisture chambers at 5, 10, 15, 20, 25 and 30° C. after treatment and inoculation.

Antibiotic activity. The possible involvement of antibiotic production in B-3 antagonism was tested as follows: The B-3 cells were separated from the culture medium by one centrifugation cycle at 6,000 X g for 20 min as previously, but a portion of the B-3 cells was resuspended in water and centrifuged a second time to wash cells and further remove any extracellular toxins. After cells were suspended again in water, a sample of the suspension with washed cells was autoclaved at 15 psi and 120° C. for 15 min. The supernatant medium from the first centrifugation cycle was passed through a 0.3 μm pore size membrane filter to eliminate any residual cells and a sample of the filtrate was autoclaved for 15 min. Fruit were teated with: Cells collected by centrifuging once; cells washed by centrifuging twice; cells killed by autoclaving the cell-free culture filtrate; and the autoclaved culture filtrate. In addition to a water control, fruit were treated with fresh NYDB medium. All fruit were inoculated as previously described.

RESULTS

All five bacterial strains inhibited radial growth of *M. fructicola* on PDA and NYDA (Table 1), with the widest zones of inhibition resulting from antagonism by the two Pseudomonas spp. These bacteria, however, had little or no effect on the pathogen in vivo (Table 2). Statistically significant differences between Pseudomonas treated fruit and control fruit were detected only with nectarines. Some reduction of decay was shown with the B-1849 strain of *B. subtilis* applied to peaches, nectarines and plums, and with *B. thuringiensis* applied to plums. The B-3 strain of *B. subtilis* had a dramatic effect on brown rot development on all fruit types. Strain B-3 prevented brown rot of peaches and apricots after 3 days and substantially reduced decay of plums and nectarines after 2 and 3 days, respectively. Benomyl prevented decay of all fruit.

Pseudomonas spp. had minimal effects on decay of peach fruit even when concentrations were increased to $10^9$ CFU per milliliter. For strains B-1849 and B-3 of *B. subtilis*, suspensions of adequate volume with concentrations higher than $10^7$ and $10^8$ CFU per milliliter, respectively, were not obtained with the growth conditions and volume of medium used. Three days after inoculation, $10^6$ CFU per milliliter of B-3 had partially reduced peach decay, $10^7$ had nearly prevented decay of most fruit, and $10^8$ had prevented decay of all fruit. After 5 days, all but two peaches sprayed with $10^7$ CFU per milliliter were rotted. After 9 days, none of the peaches treated with $10^8$ CFU per milliliter had become infected with *M. fructicola* but had succumbed to other fungi, such as *Penicillum expansum* and *Rhizopus stolonifer*.

The cell-free filtrate from the B-3 culture protected fruit from *M. fructicola* to the same extent as B-3 suspensions of $10^7$ CFU per milliliter in water (Table III). The protective ability of B-3 was decreased by washing the cells and it was completely destroyed after autoclaving the suspension. The activity of the culture filtrate was only partially lost due to autoclaving. Fruit treated with NYDB decayed at a greater rate than the control fruit sprayed with water.

DISCUSSION

Although the Pseudomonas strains were highly antagonistic to *M. fructicola* on agar media, these organisms showed minimal or no antagonism on the fruit surface. Possibly, the bacteria survived poorly on the fruit because cells from liquid culture did not have the same ability as cells grown on solid media to produce inhibitory substances, or inhibitors produced by the bacteria were unstable or inactive on the fruit surface environment.

*Bacillus thuringiensis* also did not perform well on fruit. With the *B. subtilis* strains, some activity was indicated by B-1849 in vivo, however, it was not great enough to protect the fruit. However, strain B-3 at $10^7$ CFU per milliliter actually prevented decay of peaches and apricots over a 3-day incubation period.

Biocontrol of brown rot with B-3 was more effective on peaches and apricots than on nectarines and plums. Perhaps this is related to basic differences in the fruit surfaces. One type is pubescent and the other is smooth and waxy. The hairs may improve adherence of bacteria to fruit or increase the area or number of sites on which cells may reside. It is possible that not all of the antifungal activity on fruit is due to bacterial growth and antibiotic production. Considering that washed cells were less effective (Table III), some inhibition could result from a carryover of toxic compounds such as $NH_3$, accumulated in the culture medium.

Increasing the B-3 concentration from $10^6$ to $10^7$ CFU per milliliter gave improved biocontrol, and a further increase to $10^8$ totally controlled brown rot. Higher B-3 concentrations extended the period before decay was initiated by Monilinia. Once started, however, lesions on fruit with different concentration treatments seemed to enlarge at the same rate. Apparantely, the mode of B-3 activity on fruit is toward spore germination or early germ tube development with minimal effect on subsequent fungal growth.

Antagonism of B-3 on fruit appeared to be functional at all temperatures that permitted Monilinia to decay untreated fruit. Assuming that activity is due largely to B-3 growth and antibiotic production, our results are in contrast to those of another study in which wheat seed was treated with Bacillus spp. to protect against soil fungi (Lengkeek, V. H., and Otta, J. D. 1979. "Biological Control Attempts Using Five Species of Bacillus as Seed-Treatments of Wheat". *Proc. South Dakota Acad. Sci.;* 58:144–156). The fungi grew at temperatures lower than the minimum temperature required for bacterial growth or antibiotic production. The effect of temperature on B-3 performance is of importance because fruit may be subjected to a wide temperature range between time of treatment in the packing plant and time of use by the consumer. Biological control has been demonstrated less for pathogens attacking aerial parts of plants than for those in the soil and only a few examples can be cited for this approach to the control of pathogens which directly affect the fruit. Possibly, microorganisms antagonistic to pathogens of the mature fruit or plant product have a greater potential for disease control after harvest. Many uncontrollable variables exist under the field situation, but the postharvest environment can be easily manipulated to favor the antagonist. Results reported herein demonstrate biological control of postharvest decay. The potential applications include use in commercial fruit-packing houses prior to storage or transit and in the market to prolong shelf life.

TABLE I

Bacterial Inhibition of *Monilinia fructicola* in vitro

| Bacteria | Inhibition zone (mm)[y] | |
|---|---|---|
| | PDA | NYDA |
| *Pseudomonas fluorescens* (Pf-21) | 27a[z] | 17b |
| *Pseudomonas cepacia* (Pc-41) | 22b | 20a |
| *Bacillus subtilis* (B-3) | 16c | 16bc |
| *Bacillus subtilis* (B-1849) | 14c | 15c |
| *Bacillus thuringiensis* (HD-1) | 5d | 6d |

[x]Plates were streaked across center with bacterium, sprayed with spore suspension of *Monilinia fructicola* after 2 days at 25° C., then evaluated after 3 additional days of incubation.
[y]Each value is the mean of 6 plates. PDA = potato dextrose agar; NYDA = nutrient yeast dextrose agar.
[z]Arithmetic means in a column followed by the same letter do not differ significantly at P = 0.05 by Duncan's multiple range test.

TABLE II

Postharvest Reduction of Brown Rot of Stone Fruit by Antagonistic Bacteria[x]

| Treatment | Diameter of decay lesions (mm)[y] | | | |
|---|---|---|---|---|
| | Peaches | Nectarines | Apricots | Plums |
| *Bacillus subtilis* (B-3) | 0c[z] | 7c | 0c | 4d |
| *Bacillus subtilis* (B1849) | 20b | 38b | 29b | 27c |
| *Bacillus thuringiensis* (HD-1) | 37a | 43ab | 39a | 28bc |
| *Pseudomonas cepacia* (Pc-41) | 41a | 41b | 39a | 30ab |
| *Pseudomonas fluorescens* (Pf-21) | 38a | 42b | 36ab | 29ab |
| Benomyl | 0c | 0d | 0c | 0e |
| Control | 41a | 48a | 35ab | 31a |

[x]Fruit were wounded, treated and artifically ionoculated, then incubated at 18–24° C. in moist chambers; plums were evaluated after 2 days and all other fruit after 3 days.
[y]Each value is the arithematic mean of 10 fruit.
[z]Arithmetic means in a column followed by the same letter do not differ significantly at P = 0.05 by Duncan's multiple range test.

TABLE III

Effect of *Bacillus subtilis* (B-3) Cells Suspended in Water and Cell-Free Culture Filtrate on Brown Rot of Peach[y]

| Treatment[x] | Diameter of decay lesion (mm)[y] |
|---|---|
| B-3 | 0d[z] |
| B-3 (washed) | 9c |
| B-3 (autoclaved) | 30b |
| Culture filtrate | 0d |
| Culture filtrate (autoclaved) | 9c |
| NYDB | 36a |
| Water | 30b |

[w]Fruit were wounded, treted and artificially inoculated, then incubated at 18–24° C. in a moist chamber for 3 days.
[x]B-3 suspensions consisted of cells collected by one centrifugation cycle, washed by centrifuging twice, or killed by auto-claving. Culture filtrates were obtained by passing supernatant through 0.3- m pore filter. NYDB = nutrient yeast dextrose broth.
[y]Each value is the mean of fruit.
[z]Arithmetic means in a column followed by the same letter do not differ significantly at P = 0.05 by Duncan's multiple range test.

EXAMPLE 2

Compatibility of *B. subtilis* B-3 with waxes used widely on harvested fruit to improve fruit appearance, to reduce moisture loss and to act as a carrier was tested.

The bacterium was cultured as described in Example 1. A cell suspension was prepared by centrifuging the liquid culture at 5700 RFC for 20 min, resuspending the pelleted cells in water, and centrifuging again to further remove extracellular solutes. The suspension was adjusted to approximately $10^7$ CFU per milliliter. Tests were performed with wounded and nonwounded peach fruit. Wounds were made as described in Example 1. Treatments were applied with a brush, allowed to dry for 30–60 min and then challenged with *M. fructicola* spores collected from inoculated fruit. A volume of 20 $\mu$l of the fungal spore suspension ($10^5$ conidia per milliliter) was placed in the wound or on the fruit surface. On nonwounded fruit the suspenison drop formed a small bead which evaporated or was absorbed by the fruit in 1–2 hr. A total of 10 fruit were used per treatment. The fruit were separated so that all treatments were represented in a randomized design. The fruit were then incubated at 20° C. and 70–100% RH. After various periods of incubation, disease development was determined based on lesion diameter. Figures for wounded fruit were corrected by subtracting the 3.0 mm wound diameter. When fruit were totally decayed, lesion diameters of 222 and 225 mm were used for wounded and nonwounded fruit, respectively, based on an estimated average fruit circumferance. Natural infection by Rhizopus and other fungi warranted removal of some fruit from the test. Data were analyzed using Waller-Duncan K-ratio t test (p=0.05).

The bacterial preparations were tested on fruit in combination with four different waxes commonly applied to fruit in commercial packing houses. Two of the waxes, both consisting of a paraffin mineral oil base, were obtained from Durand-Wayland, Inc., La Grange, GA (Special Peach, Plum and Nectarine Wax Coating), and Freshmark Chemical Co., Orlando, FL (Fresh Wax 58P). Two Water-based waxes were from Decco Tiltbelt. Division,Pennwalt Corporation, Monrovia, CA, (Peach, Plum, and Nectarine Lustr 251) and FMC Corp., Woodstock, VA, (Stafresh 707 Fruit Wax). Bacterial preparations were applied separately 1–2 hr prior to wax application or mixed with the wax (1:1;V/V) and applied at the same time. Combinations involving the aqueous bacterial preparations and oil-based wax were continually agitated to maintain a mixture during application to both wounded and nonwounded fruit.

Results

All waxes on nonwounded fruit and all except the FMC wax on wounded fruit reduced decay caused by *M. fructicola* (Table IV), but treatments with the B-3/wax mixture always resulted in less decay than with wax alone. Usually, the mixtures were effective as B-3 applied alone, but sometimes greater decay developed when B-3 was mixed with wax. The negative effect was shown with both oil and water-based waxes, but more frequently with the latter.

Discussion

We would not have expected a bacterium such as *B. subtilis* to undergo normal respiration when covered with or incorporated into a wax (consisting of either a water or paraffin/mineral oil base) since the organism does not grow anaerobically according to Gordon etal., "The Genus Bacillus", Agriculture Handbook No. 27, ARS-USDA, Washington, D.C., U.S. Government Printing Office, October 1973, pages 41 and 248. Although wax sometimes had a negative effect on B-3, the B-3/wax mixture always reduced decay as compared to check fruit. Thus, *B. subtilis* B-3 can be incorporated for brown rot control into a commercial fruit-packing operation in which wax is already employed. The organism might be applied prior to waxing, during waxing, or without waxing and still provide protection against *M. fructicola*.

TABLE IV

Compatibility of *Bacillus subtilis* B-3 for peach brown rot control with commercial postharvest waxes

| Treatment | Lesion diameter (mm)[y] | | | |
|---|---|---|---|---|
| | Wounded | | Non wounded | |
| | Separate | Mixed | Separate | Mixed |
| Water | 71[z] | 85 | 150 | 163 |
| DW Wax | 52 | 62 | 87 | 43 |
| FC Wax | 49 | 50 | 112 | 46 |
| DT Wax | 71 | 81 | 43 | 89 |
| B-3 | 12[z] | 18 | 0 | 0 |
| B-3 + DW Wax | 13 | 11 | 6 | 8 |
| B-3 + FC Wax | 6 | 35 | 0 | 1 |
| B-3 + DT Wax | 17 | 42 | 1 | 0 |
| B-3 + FMC | 20 | 47 | 0 | 1 |
| LSD (P = 0.05) | 13.9 | 11.0 | 7.7 | 6.1 |

[x]B-3 was tested on fruit alone and in combination with: oil-based waxes produced by Durand-Wayland, Inc. (DW) and Freshmark Chemical Co. (FC); and water-based waxes produced by Deco Tiltbelt Division of Pennwalt Corp. (DT) and FMC Corp. (FMC).
[y]B-3 and wax were applied separately (the former 1-2 hr before the latter) or as a mixture. Wounded and nonwounded fruit were incubated 6 and 9 days, respectively.
[z]Value is arithmetic mean of 5-7 fruit; all other values in table are arithmetic means of B-10 fruit.

Example 3

Generally, different fungicides are used on harvested stone fruit for controlling the major diseases, brown rot and rhizopus rot (caused by Rhizopus spp.) Commonly, benomyl is used for the former and dicloran (2,6-dichloro-4-nitroaniline) for the latter. Since *B. subtilis* (B-3) is ineffective against Rhizopus, compatibility of B-3 with dicloran was tested.

Materials and Methods

Procedures were the same as in Example 2 except where indicated wounded; fruit were treated with B-3 mixed with dicloran. Final concentration of dicloran was at 899 mg per liter. Oil-based wax was mixed with one volume water (as a check) or one volume of the aqueous bacterial suspension by constant agitation with a magnetic stirrer. The experiment was performed three times with oil-based wax and once with water based wax. Incubation was at 25° C. for the first experiment and 20° C. for the second. In the later test fruit received the above treatments but were challenged with 20 μl of a $10^5$ spores per millimeter suspension of Rhizopus sp. (obtained from decayed peach fruit at Byron, GA) rather than *M. fructicola*.

Results

Although oil-based wax had some negative effect on B-3 activity, dicloran contributed to less decay. In the test with oil-based wax neither dicloran nor B-3 were extremely effective in protecting wounded fruit from *M. fructicola* but a combination of the two provided total protection during 3 days of incubation (Table V). Strain B-3 did not effect Rhizopus but dicloran or all combinations which included dicloran provided total or almost total protection against Rhizopus during 2 days of incubation.

When water-based wax was substituted for oil-based wax, dicloran again counteracted the negative effect of wax on B-3 as shown after 9 days incubation (shown in FIG. 1). Also, the B-3/dicloran mixture was again more effective than earlier dicloran or B-3 alone and the B-3/dicloran/wax mixture was more effective than either mixtures of dicloran/wax or B-3/wax.

Discussion

The data indicate that B-3 could be mixed with dicloran and applied to fruit in a commercial fruit-packing house for the purpose of controlling fungal decay. The greater effectiveness of the B-3/dicloran mixture as compared to either agent applied alone was totally unexpected because the B-3 strain of *B. subtilis* was not expected to be compatible with the microbicide, dicloran.

TABLE V

Compatibility of *Bacillus subtilis* (B-3) for postharvest brown rot control with dicloran and oil-based wax[x]

| Treatment | Lesion diameter (mm)[y] | |
|---|---|---|
| | Monilinia | Rhizopus |
| Water | 49 | 67 |
| Wax | 37 | 32 |
| Dicloran | 17 | 0 |
| Dicloran + wax | 18 | 3 |
| B-3 | 18 | 66 |
| B-3 + wax | 26 | 40 |
| B-3 + dicloran | 0 | 0 |
| B-3 + dicloran + wax | 0 | 1 |
| LSD (F = 0.05) | 2.8 | 6.0 |

[x]oil-based wax was obtained from Durand-Wayland, Inc.
[y]wounded fruit were challenged with *Monilina fruicticola* or Rhizopus sp. and incubated for 3 and 2 days, respectively, Values for Monilina represent arithematic means of 289-30 fruit and values for Rhizopus represent 10 fruit.

EXAMPLE 4

Prior to or during the period fruit are being marketed, they are generally stored in a low-temperature environment. Tests were conducted to determine whether strain B-3 of *B. subtilis* would retain its ability to protect against brown rot under such conditions.

Materials and Methods

Procedures were the same as in Example 2 except where indicated. Nonwounded peach fruit were treated and held in a low-temperature environment (2-4° C. and 70-100% RH) for up to 21 days prior to the fungal-spore challenge and high-temperature incubation. A rifampicin-resistant isolate, derived from B-3 using the procedure of Kloepper et al, was used in fruit treatments to facilitate positive identification of the organism following storage and incubation. The isolate was maintained on NYDA containing 50 μl/ml rifampicin. Strain B-3 oil based wax was applied as a one to one mixture. For water-based wax, to obtain the recommended one to three dilution with water, the mixture was made up with two parts of the B-3 suspension, one part wax and one part water. Final concentration of dicloran was at 899 mg per liter.

Results

Fruit treated with B-3 were free of decay after 0.7 and 14 days in storage (Table VI); after 21 days, fruit showed minimal decay equivalent to that of benomyl-treated fruit.

Discussion

The effect of fruit-storage conditions on strain B-3 of *B. subtilis* was not predictable since no comparable system had been tested before. The organism would probably survive on the fruit surface in the form of spores, but would antifungal activity resume when fruit were brought out of the low-temperature environment and subjected to high-temperature conditions conducive to fungal decay? Test results indicate yes and further demonstrate the suitability of strain B-3 for post-harvest control of brown rot.

TABLE VI

Retention of *Bacillus subtilis* (B-3) activity against brown rot under simulated cold-storage conditions.[x]

| Treatment[y] | Lesion diameter (mm)[z] | | | |
|---|---|---|---|---|
| | 0 days | 7 days | 14 days | 21 days |
| Water | 70 | 44 | 68 | 121 |
| B-3 | 0 | 0 | 0 | 3 |
| Benomyl | 1 | 0 | 0 | 1 |
| LSD (P = 0.05) | 7.5 | 6.2 | 6.1 | 26.9 |

[x]Following treatment of nonwounded peaches, the fruit were held at 2–4° C. for periods of 0–21 days before fungal-spore challenge and incubation in moist chamber at 20° C. for 6 days.
[y]Benomyl was applied at 300n mg per liter.
[z]Values are arithematical means of 10 fruit.

EXAMPLE 5

A preliminary pilot test was conducted on a simulated commercial fruit-packing line at Clemson University in July of 1985. This was done to assess whether the biological control system using *B. subtilis* (B-3) would be efficacious in controlling brown rot in a commercial operation.

Materials and Methods

The B-3 strain of *Bacillus subtilis* was cultured as described previously. The bacterial cells were separated from the culture by centrifugation at 5520 RFC for 20 min and then resuspended in water to a concentration of $10^7$ colony forming units per milliliter. Firm, ripe, Redglove peaches were floated in a dump tank to which 12 rotted fruit covered with spores of the brown rot fungus were previously added to serve as a source of inoculum. The fruit were moved onto a conveyor, defuzzed in a spray wash with brushes, dried on polyurethane drying rolls, and sprayed with the treatment suspension as the fruit passed over another set of brushes. The spray system for applying the treatment was made up of two 26B nozzles in sequence with fluid cap 40100 and air cap 140-6-37-70 degrees. Each nozzle delivered 8 ml of suspension per minute.

Three parts of the B-3 aqueous suspension were added to one part water or one part undiluted wax. The wax used was Peach, Plum and Nectarine Lustr 251 (3:1 dilution with water), a product of Decco Tiltbelt Division of Pennwalt Corp. Dicloran (active ingredient of Botran 75 W) at a final concentration of 899 mg per liter was combined with B-3 for Rhizopus control and benomyl (active ingredient of Benlate 50W) at 300 mg per liter was included in the test as a standard fungicide treatment for brown rot control. Each treatment was replicated four times, using 100 fruit per replicate. Treated fruit were packed in fiber trays which were placed in cardboard boxes and then held at 22°–25° C.

Results

The B-3 strain appeared to reduce decay when applied alone or in combination with dicloran (Table VII). Its effect when applied was not as apparent since wax itself provided some protection. After 8 days the combined effect of B-3 and dicloran was greter than the effect of either applied alone.

Discussion

In contrast to previous experiments in the laboratory with small volumes of fruit, (Examples 1–4), the present test was conducted with relatively large volumes of fruit which were treated with equipment of the same type used in commercial fruit-packing houses. Since the standard fungicide (bnenomyl) did not perform as expected, rate of application was thought to be too low. (A residue analysis was not performed in this preliminary test.) Possibly also, the fruit were overwhelmed with the fungal inoculum.

The B-3 strain reduced brown rot when applied alone or when mixed with dicloran. As in laboratory experiments, the combined effect of B-3 and dicloran after 8 days was greater than that of either agent applied alone. The test showed that *B. subtilis* (B-3) could be used in a postharvest commercial operation to reduce the incidence of brown rot.

TABLE VII

Application of *Bacillus subtilis* B-3 for brown rot control on simulated commercial fruit-packing line

| Treatment[y] | % Brown rot[z] | |
|---|---|---|
| | 4 days | 8 days |
| Water | 46 | 85 |
| B-3 | 6 | 50 |
| Dicloran | 39 | 71 |
| Dicloran + wax | 9 | 44 |
| Dicloran + benomyl | 28 | 68 |
| Dicloran + benomyl + wax | 4 | 28 |
| Dicloran + B-3 | 6 | 28 |
| Dicloran + B-3 + wax | 3 | 22 |

[y]Final concentrations of dicloran and benomyl were 899 and 300 mg per liter, respectively. Water based wax from Decco Tiltbelt Division of Pennwalt Corp. was used at 3:1 dilution.
[z]Fruit were evaluated after 4 and 8 days at 22–25° C. Values are arithmetic means of four replicates, using 100 fruit per replicate.

We claim:

1. A method for biologically controlling or inhibiting brown rot on postharvest stone fruit comprising: coating the postharvest stone fruit with an effective amount of *Bacillus subtilis* B-3 bacteria to prevent or control brown rot of the fruit.

2. The method of claim 1 wherein the fruit is selected from the group consisting of: peaches, nectarines, plums, and apricots.

3. The method of claim 1 wherein the fruit is coated with an effective amount of a mixture of *B. subtilis* B-3 bacteria and 2,6-dichloro-4-nitroaniline to control or prevent brown rot of the fruit.

4. The method of claim 1 wherein the fruit is coated with an effective amount of a mixture of *B. subtilis* B-3 and wax to prevent or control brown rot of the fruit.

5. The method of claim 1 wherein the fruit is coated with an effective amount of a mixture of *B. subtilis* B-3 and paraffin and mineral oil base to prevent or control brown rot of the fruit.

6. The method of claim 5 wherein the mixture contains concentrations of *B. subtilis* B-3 of from about $10^7$ to $10^8$ CFU.

7. The method of claim 6 wherein the *B. subtilis* B-3 is grown in a culture medium and the fruit is treated with the culture medium containing *B. subtilis*.

8. The method of claim 6 wherein the *B. subtilis* B-3 is separated out of the culture medium and the culture medium is used to treat the fruit for prevention or control of brown rot.

9. The method of claim 7 wherein the *B. subtilis* B-3 bacteria in the mixture is applied in concentrations of from about $10^6$ to $10^7$ to colony forming units CFU.

10. The method of claim 7 wherein the *B. subtilis* B-3 bacteria is separated out of the culture medium, washed and resuspended in water, and then applied to the fruit to prevent or control brown rot.

* * * * *